United States Patent
Zhang et al.

(10) Patent No.: US 7,927,893 B2
(45) Date of Patent: Apr. 19, 2011

(54) METHOD FOR TREATMENT OF SAMPLES FOR AUGER ELECTRONIC SPECTROMETER (AES) IN THE MANUFACTURE OF INTEGRATED CIRCUITS

(75) Inventors: Qi Hau Zhang, Shanghai (CN); Ming Li, Shanghai (CN); Chorng Shyr Niou, Shanghai (CN); Scott Liao, Shanghai (CN)

(73) Assignee: Semiconductor Manufacturing International (Shanghai) Corporation, Shanghai (CN)

( * ) Notice: Subject to any disclaimer, the term of this patent is extended or adjusted under 35 U.S.C. 154(b) by 10 days.

(21) Appl. No.: 12/364,977

(22) Filed: Feb. 3, 2009

(65) Prior Publication Data

US 2009/0305440 A1 Dec. 10, 2009

Related U.S. Application Data (63) Continuation of application No. 11/378,400, filed on Mar. 16, 2006, now Pat. No. 7,504,269.

(30) Foreign Application Priority Data

Dec. 27, 2005 (CN) .......................... 2005 1 0133003

(51) Int. Cl.
H01L 21/66 (2006.01)
(52) U.S. Cl. ........................................................ 438/14
(58) Field of Classification Search ............... 438/14–18
See application file for complete search history.

(56) References Cited

U.S. PATENT DOCUMENTS

| | | | |
|---|---|---|---|
| 7,504,269 B2 | 3/2009 | Zhang et al. | |
| 2002/0123161 A1 | 9/2002 | Ushiki et al. | |
| 2003/0073278 A1* | 4/2003 | Ohmi et al. | .................... 438/225 |
| 2004/0159944 A1 | 8/2004 | Datta et al. | |
| 2005/0017355 A1 | 1/2005 | Chou et al. | |
| 2005/0272244 A1 | 12/2005 | Wada | |

OTHER PUBLICATIONS

Carlson, "Auger Electron Spectroscopy." *Photoelectron and Auger Spectroscopy*, Ch. 6, Sections 4.1 and 4.4, pp. 314-317, 321-332. Plenum Press: New York, 1975.
Joshi et al., "Auger Electron Spectroscopy." *Methods of Surface Analysis*, Czanderna, ed. Ch. 5, Section V, pp. 187-222. Elsevier Scientific Publishing Co: Amsterdam, The Netherlands, 1975.

(Continued)

*Primary Examiner* — Thanh V Pham
*Assistant Examiner* — Tony Tran
(74) *Attorney, Agent, or Firm* — Kilpatrick Townsend and Stockton LLP (57) ABSTRACT

A method for analyzing a sample for the manufacture of integrated circuits, e.g. MOS transistors, application specific integrated circuits, memory devices, microprocessors, system on a chip. The method includes providing an integrated circuit chip, which has a surface area with at least one region of interest, e.g., bond pad. The method includes covering a first portion of the surface area including the region of interest using a blocking material. The method also forms a metal layer on a second portion of the surface area, while the blocking material protects the first portion. The method removes the blocking material to expose the first portion of the surface area including the region of interest. The method also subjects the metal layer to a voltage differential to draw away one or more charged particles from the first portion of the surface area. The method also subjects the surface area including the region of interest to spectrometer analysis.

10 Claims, 10 Drawing Sheets

OTHER PUBLICATIONS

Morabito et al., "The use of Auger electron spectroscopy and secondary ion mass spectrometry in the microelectronic technology." *Method of Surface Analysis*, Czanderna, ed. Ch. 7, Section XIV(D), p. 323. Elsevier Scientific Publishing Co: Amsterdam, The Netherlands, 1975.

Notice of Allowance for U.S. Appl. No. 11/378,400, mailed on Nov. 4, 2008, 7 pages.

Final Office Action for U.S. Appl. No. 11/378,400, mailed on Apr. 29, 2008, 11 pages.

Non-Final Office Action for U.S. Appl. No. 11/378,400, mailed on Nov. 1, 2007, 9 pages.

* cited by examiner

With Al foil, before coating

With Al foil, after coating 4 nin

After coating and Al foil being removed

METHOD FOR TREATMENT OF SAMPLES FOR AUGER ELECTRONIC SPECTROMETER (AES) IN THE MANUFACTURE OF INTEGRATED CIRCUITS

CROSS-REFERENCES RO RELATED APPLICATIONS

This application is a continuation of U.S. patent application Ser. No. 11/378,400 filed Mar. 16, 2006, which claims priority to Chinese Application No. 200510133003.3, filed on Dec. 27, 2005, commonly assigned; both applications are hereby incorporated by reference for all purposes.

BACKGROUND OF THE INVENTION

The present invention is directed to integrated circuits and their processing for the manufacture of semiconductor devices. More particularly, the invention provides a method and apparatus for preparing samples for an Auger Electronic Spectrometer for the manufacture of integrated circuit devices, but it would be recognized that the invention has a much broader range of applicability. As merely an example, these sample preparation techniques can lead to identifying particulate contamination and/or residues, which lead to lower device yields and other reliability problems.

Integrated circuits have evolved from a handful of interconnected devices fabricated on a single chip of silicon to millions of devices. Conventional integrated circuits provide performance and complexity far beyond what was originally imagined. In order to achieve improvements in complexity and circuit density (i.e., the number of devices capable of being packed onto a given chip area), the size of the smallest device feature, also known as the device "geometry", has become smaller with each generation of integrated circuits.

Increasing circuit density has not only improved the complexity and performance of integrated circuits but has also provided lower cost parts to the consumer. An integrated circuit or chip fabrication facility can cost hundreds of millions, or even billions, of U.S. dollars. Each fabrication facility will have a certain throughput of wafers, and each wafer will have a certain number of integrated circuits on it. Therefore, by making the individual devices of an integrated circuit smaller, more devices may be fabricated on each wafer, thus increasing the output of the fabrication facility. Making devices smaller is very challenging, as each process used in integrated fabrication has a limit. That is to say, a given process typically only works down to a certain feature size, and then either the process or the device layout needs to be changed. Additionally, as devices require faster and faster designs, process limitations exist with certain conventional processes and materials.

An example of a process that has limitations based upon a given feature size is the formation of bond pad structures for integrated circuits. Such bond pad structures are often formed using aluminum metal layers, which are patterned using photolithography techniques. Such aluminum metal layers often become contaminated with residual particles and/or other impurities. These particles and/or impurities lead to lower device yields and other reliability problems. These and other limitations of integrated circuits can be found throughout the present specification and more particularly below.

From the above, it is seen that an improved technique for processing semiconductor devices is desired.

BRIEF SUMMARY OF THE INVENTION

According to the present invention, techniques for processing integrated circuits for the analysis of semiconductor devices are provided. More particularly, the invention provides a method and apparatus for preparing samples for an Auger Electronic Spectrometer for the manufacture of integrated circuit devices, but it would be recognized that the invention has a much broader range of applicability. As merely an example, these sample preparation techniques can lead to identifying particulate contamination and/or residues, which lead to lower device yields and other reliability problems.

In a specific embodiment, the present invention provides a method for analyzing a sample for the manufacture of integrated circuits, e.g. MOS transistors, application specific integrated circuits, memory devices, microprocessors, system on a chip. The method includes providing an integrated circuit chip, the integrated circuit chip having a pad area surrounded by passivation material. The pad area has at least one region of interest. In a specific embodiment, the term "surrounded" can mean entirely or partially and should not depart from its ordinary meaning. In a preferred embodiment, the pad area has an exposed bond pad, which is made substantially of aluminum bearing material. The method includes covering a first portion of the pad area including the region of interest using a blocking material. The method includes forming a metal layer on a second portion of the pad area, while the blocking material protects the first portion. The method also includes removing the blocking material to expose the first portion of the pad area including the region of interest. The method subjects the metal layer to a voltage differential to draw away one or more charged particles from the first portion of the pad area and also subjects the pad area including the region of interest to spectrometer analysis.

In an alternative specific embodiment, the present invention provides a method for analyzing a sample for the manufacture of integrated circuits, e.g. MOS transistors, application specific integrated circuits, memory devices, microprocessors, system on a chip. The method includes providing an integrated circuit chip, which has a surface area with at least one region of interest, e.g., bond pad. The method includes covering a first portion of the surface area including the region of interest using a blocking material. The method also forms a metal layer on a second portion of the surface area, while the blocking material protects the first portion. The method removes the blocking material to expose the first portion of the surface area including the region of interest. The method also subjects the metal layer to a voltage differential to draw away one or more charged particles from the first portion of the surface area. The method also subjects the surface area including the region of interest to spectrometer analysis.

In yet an alternative specific embodiment, the present invention provides an apparatus for treatment of a sample for the manufacture of integrated circuits. The apparatus has a holder apparatus. A stage is coupled to the holder apparatus. In a preferred embodiment, the stage is capable of holding a portion of a sample to be analyzed. The apparatus also has a shield operably coupled to the stage to block a portion of the sample. The shield is capable of movement relative to the sample to block one or more portions of the sample. In a specific embodiment, the shield is provided on a track member and is movable from a first spatial location to a second spatial location on the track member.

In a specific embodiment, the term "Auger electron spectroscopy (AES)" is used according to one of ordinary skill in the art. The term AES is a technique that can be used to identify elemental compositions of surfaces by detecting energies of Auger electrons, which are interpreted under ordinary meaning. In a specific embodiment, the Auger electron emission is generally stimulated by bombarding the sample with an electron beam. The Auger electron energies are characteristic of the elements from which the electrons are derived. Auger electron spectroscopy can be used for analysis of surfaces, thin films, and interfaces according to a specific embodiment. Further details of techniques using AES can be found in "Photoelectron and Auger Spectroscopy," T. A. Carlson (Plenum Press, New York, 1975) and "Methods of Surface Analysis," A. W. Czanderna, ed. (Elsevier, New York, 1975), among other sources.

Many benefits are achieved by way of the present invention over conventional techniques. For example, the present technique provides an easy to use process that relies upon conventional technology. In some embodiments, the method provides higher device yields in dies per wafer. Additionally, the method provides a process that is compatible with conventional process technology without substantial modifications to conventional equipment and processes. Preferably, the invention provides for an improved technique to identify particular contamination and/or residues that can lead to device failure and/or other reliability issues according to a specific embodiment. Depending upon the embodiment, one or more of these benefits may be achieved. These and other benefits will be described in more throughout the present specification and more particularly below.

Various additional objects, features and advantages of the present invention can be more fully appreciated with reference to the detailed description and accompanying drawings that follow.

DETAILED DESCRIPTION OF THE INVENTION

According to the present invention, techniques for processing integrated circuits for the manufacture of semiconductor devices are provided. More particularly, the invention provides a method and apparatus for preparing samples for an Auger Electronic Spectrometer for the manufacture of integrated circuit devices, but it would be recognized that the invention has a much broader range of applicability. As merely an example, these sample preparation techniques can lead to identifying particulate contamination and/or residues, which lead to lower device yields and other reliability problems.

As background information, we have discovered that pad surface quality is a frequently monitored item in a semiconductor foundry. That is, pad surface quality is often monitored for contamination or residues on pad surface, which often bring about a series of bonding issues such as bondability and poor electrical contact. Among the many surface analysis tools, AES (Auger Electronic Spectrometer) is often used for pad surface composition analysis due to its features of surface sensitivity (e.g., top 3~50 Angstroms), better spatial resolution, and quick identification of elements. Many limitations exist with AES as device sizes become smaller and smaller.

As merely an example, charging effects, which often result in the shift of element peaks or even severe distortion of the acquired spectrum, are a problem that AES analysis would face during pad analysis. It is also known that AES identifies elements by their specific Auger electron peak positions and electron beam is the excited source of Auger electrons. When primary electron beam scans over the surface of pads and surrounding passivation layer, because most pads in chips are not grounded and the passivation materials are not electricity conducting either, large amount of electrons can be accumulated on such surface and form a negative potential, which will impede the escape of Auger electrons from the pad surface and cause the charging effect mentioned previously.

In the past, several methods have been developed in an attempt to reduce the charging effect that AES analysis encounters. Some of them include coating platinum (Pt) on entire sample surfaces, enveloping samples with aluminum foil, irritating sample surface with low energy ion and so on. Unfortunately, each of these methods has its own shortcoming. For example, Pt coating may damage the analyzed surface or the signals of the elements really existing on the surface can be weakened or interfered by the numerous Pt signal peaks. Enveloping certain structures using aluminum foil has low success rate. Low energy ion neutralization often requires additional expenses. In a specific embodiment, we present a method and apparatus for AES analysis to reduce charging effect during AES analysis, which is easy, cost effective, efficient, and has substantially no damage to the analyzed surface in the manufacture of integrated circuits. Further details of the present method and apparatus can be found throughout the present specification and more particularly below.

Figure 1:
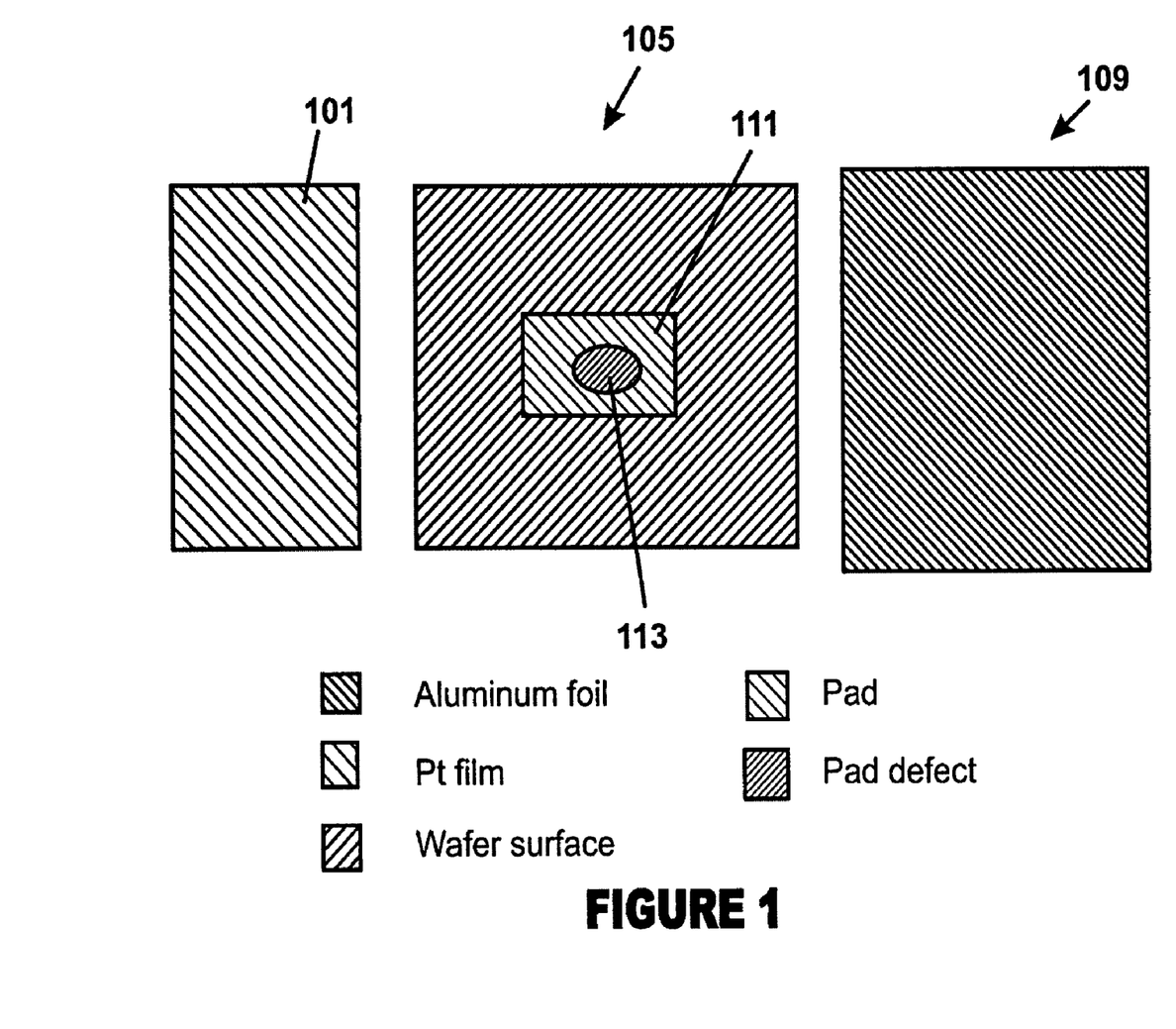
FIG. 1 is a simplified diagram illustrating a top-view of a patterned metal layer according to an embodiment of the present invention.
Figure 1A:
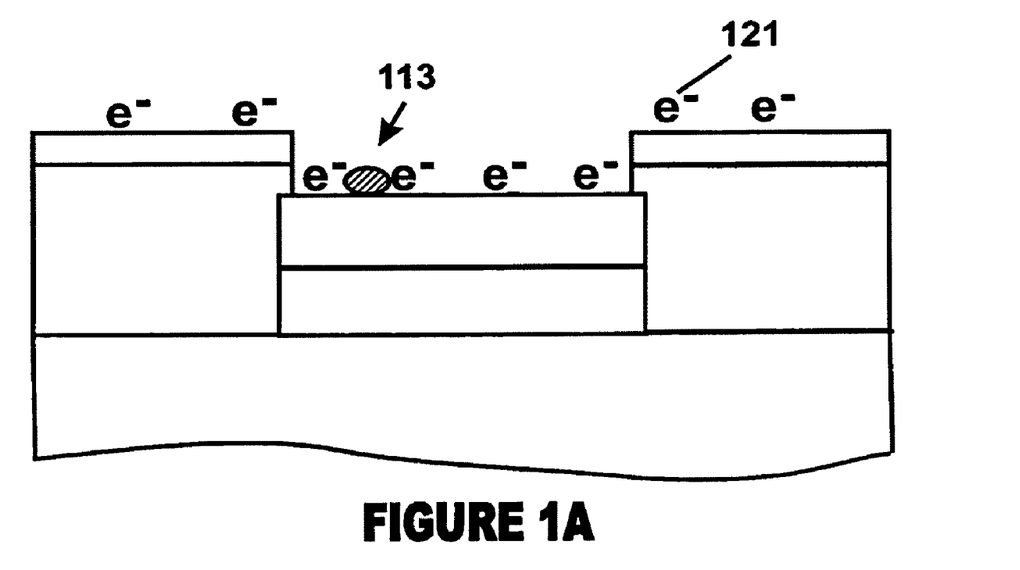
FIGS. 1A and 1B are simplified side-view and top-view diagrams of a patterned metal layer according to an embodiment of the present invention.
Figure 1B:
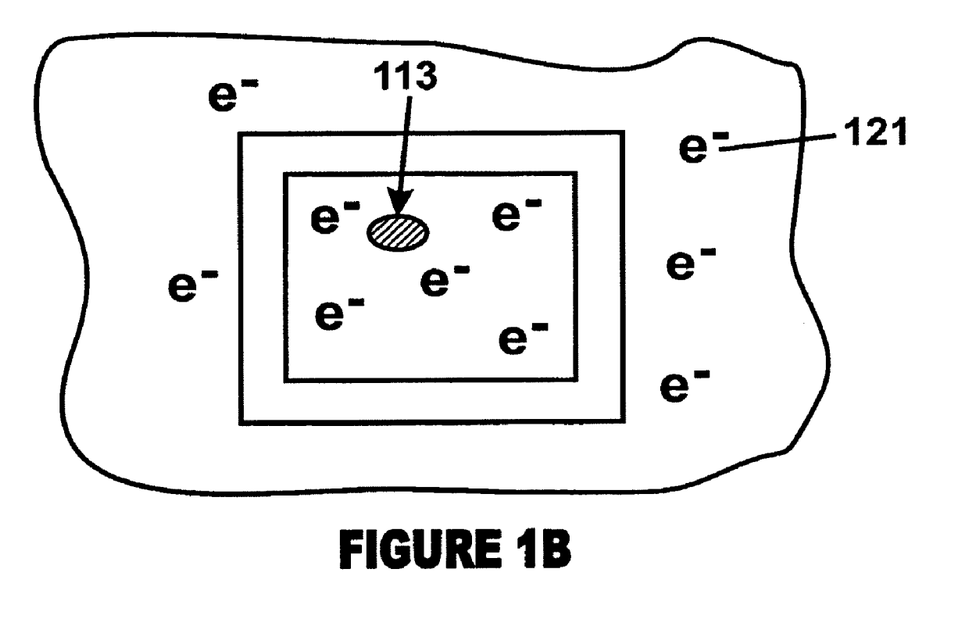

FIG. 1 is a simplified diagram illustrating a top-view 105 of a patterned metal layer according to an embodiment of the present invention. This diagram is merely an example, which should not unduly limit the scope of the claims herein. One of ordinary skill in the art would recognize many variations, modifications, and alternatives. As shown, the top-view patterned metal layer includes pad region 111, which includes a pad defect 113 or defects. In a specific embodiment, the pad region includes an aluminum bonding pad or other like structure. The defect can be any particulate contamination and/or residues according to a specific embodiment. The patterned metal layer is provided on a semiconductor substrate, which includes an overlying surface region, according to a specific embodiment. The present invention uses a platinum film 101 and aluminum foil, which serves as a blocking layer, according to a specific embodiment. Referring to FIGS. 1A and 1B, the present method reduces an influence of electrons 121, which are overlying the surfaces including the pad region and peripheral region, of the patterned metal layer. Further details of the present method can be found throughout the present specification and more particularly below.

A method for analyzing an integrated circuit device, including a testing method, according to an embodiment of the present invention may be outlined as follows.

1. Provide an integrated circuit chip, the integrated circuit chip having a pad area surrounded by passivation material;

2. Cover a first portion of the pad area including a region of interest using a blocking material;
3. Form a metal layer on a second portion of the pad area, while the blocking material protects the first portion;
4. Remove the blocking material to expose the first portion of the pad area including the region of interest;
5. Subject the metal layer to a voltage differential to draw away one or more charged particles from the first portion of the pad area;
6. Subject the pad area including the region of interest to spectrometer analysis; and
7. Perform other steps, as desired.

The above sequence of steps provides a method according to an embodiment of the present invention. As shown, the method uses a combination of steps including a way of testing a pad area for defects using an AES analysis technique for the manufacture of integrated circuits. Other alternatives can also be provided where steps are added, one or more steps are removed, or one or more steps are provided in a different sequence without departing from the scope of the claims herein. Details of the present method and structure can be found throughout the present specification and more particularly below.

Figure 2:
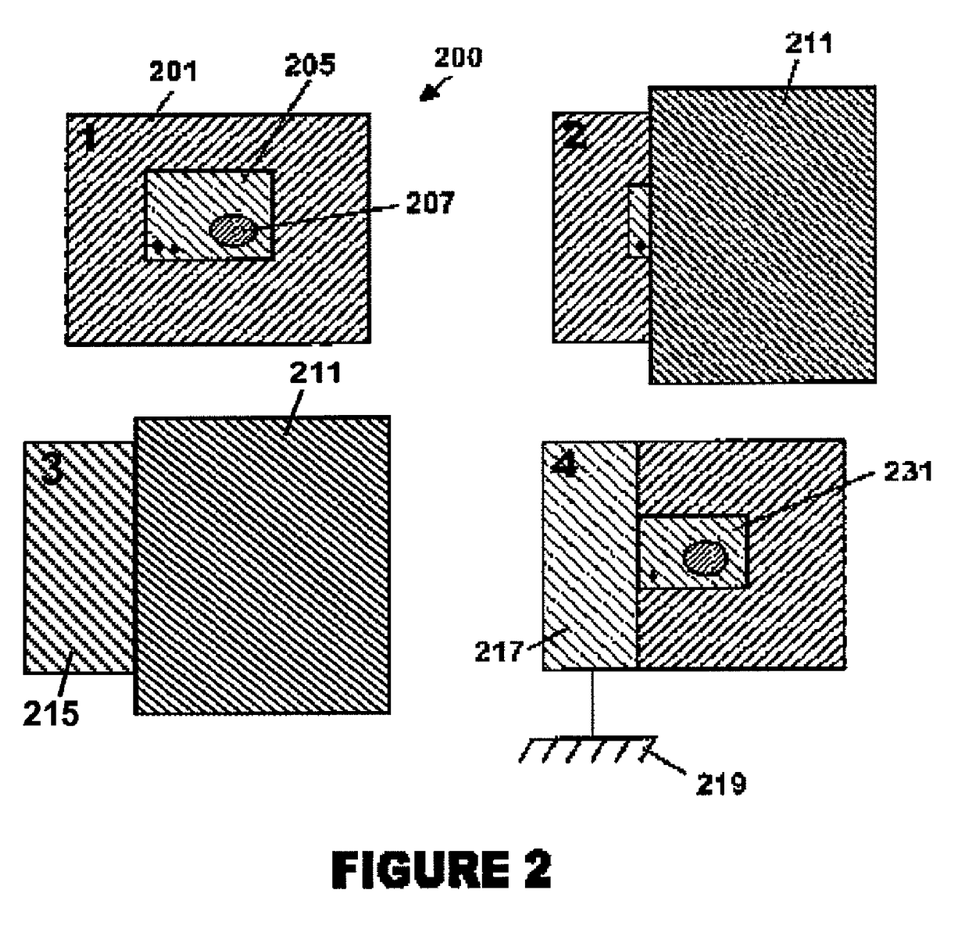
FIG. 2 is a simplified diagram illustrating a method of processing a patterned metal layer according to an embodiment of the present invention.

FIG. 2 is a simplified diagram illustrating a method of processing a patterned metal layer according to an embodiment of the present invention. This diagram is merely an example, which should not unduly limit the scope of the claims herein. One of ordinary skill in the art would recognize many variations, modifications, and alternatives. In a specific embodiment, the present invention provides a method for analyzing a sample 200 for the manufacture of integrated circuits, e.g. MOS transistors, application specific integrated circuits, memory devices, microprocessors, system on a chip. The method includes providing an integrated circuit chip. The integrated circuit chip has a pad area 205 surrounded by passivation material 201. In a specific embodiment, the passivation material can include an oxide layer with an overlying silicon nitride layer. The pad area has at least one region of interest, which will be tested using an AES technique. In a specific embodiment, the term "surrounded" can mean entirely or partially and should not depart from its ordinary meaning. In a preferred embodiment, the pad area has an exposed bond pad, which is made substantially of aluminum bearing material. Of course, there can be other variations, modifications, and alternatives.

In a specific embodiment, the pad area includes one or more defects 207. The one or more defects can include a residual material and/or particulate contamination according to a specific embodiment. The particulate contamination can be neutral and/or charged depending upon the specific embodiment. The particulate contamination can have a size ranging from about 0.5 micron 0.05 to about a deep submicron level and less. Of course, there can be other variations, modifications, and alternatives.

Referring again to FIG. 2, the method includes covering a first portion of the pad area including the region of interest using a blocking material 211. The blocking material can be any shielding material, which can block exposure of the first portion of the pad area, which includes the one or more defects. In a specific embodiment, the blocking material is a sheet of aluminum bearing material or other like material. Of course, there can be other variations, modifications, and alternatives.

The method includes forming a metal layer 215 on a second portion of the pad area, while the blocking material protects the first portion. In a specific embodiment, the metal layer can be any suitable conductive material such as platinum, chromium, carbon, and other material and/or materials. In a preferred embodiment, the platinum is a thin layer having a thickness of about 50 Angstroms and less. In a specific embodiment, the platinum is often formed using a sputtering process.

The method also includes removing the blocking material to expose the first portion of the pad area including the region of interest 231. As shown, the region of interest includes the one or more defects according to a specific embodiment. The method subjects the metal layer 217, which has been formed, to a voltage differential 219 to draw away one or more charged particles from the first portion of the pad area. Once the electrons have been drawn away, the method subjects the pad area including the region of interest to spectrometer analysis. Since the electrons have been substantially eliminated, the AES analysis is free from any improper readings and the like from such electrons. Of course, there can be other variations, modifications, and alternatives.

Figure 2A:
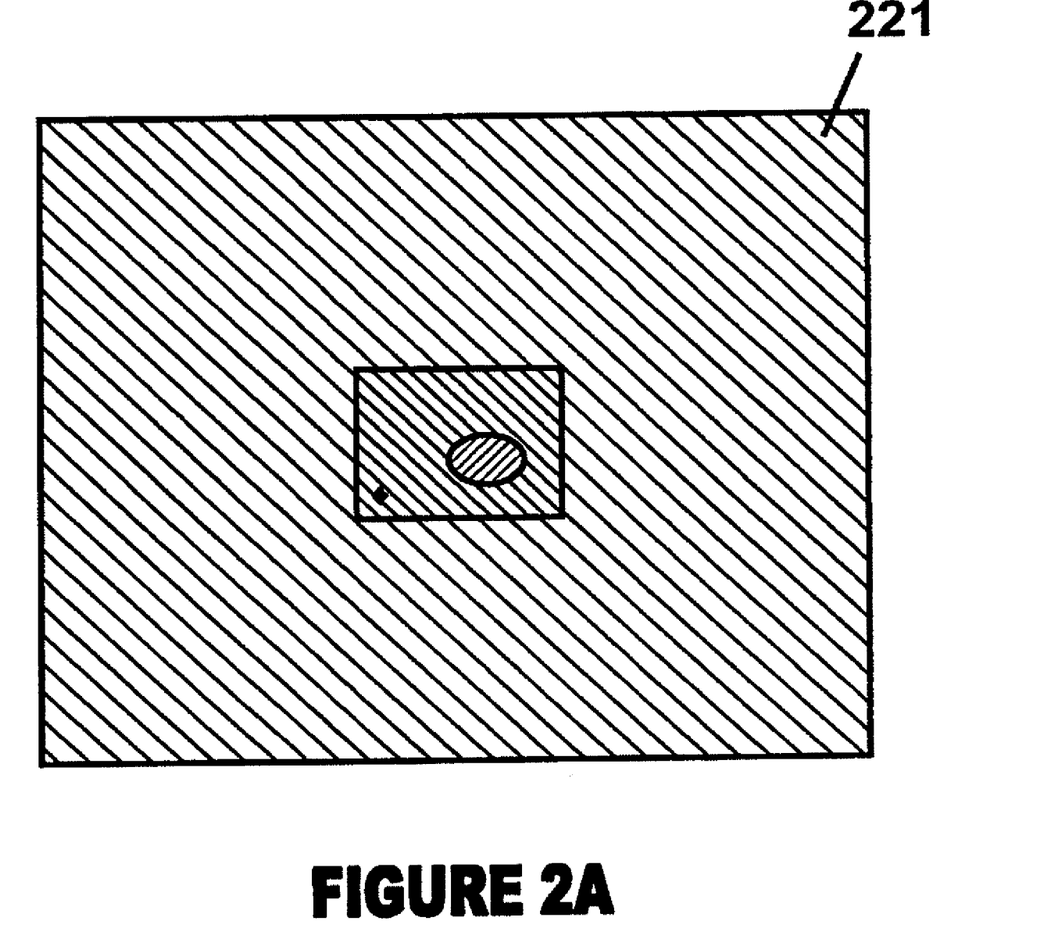
FIG. 2A is a simplified top-view diagram of a patterned metal layer including a defect according to an embodiment of the present invention.

In a specific embodiment, the method can also repeat one or more of the steps above to reduce and/or eliminate any of the charging influences. That is, in order to eliminate the charging effect from the surrounding passivation material, the present method can be repeated on the other three spatial directions (e.g., rotate 90, 180, and 270 degrees in turn) and form a squared analyzed area free of platinum coating on the pad, as shown in FIG. 2A. As shown, surrounding area 221 includes a metal coating, while the pad area is free from such metal coating, according to a specific embodiment.

Figure 3:
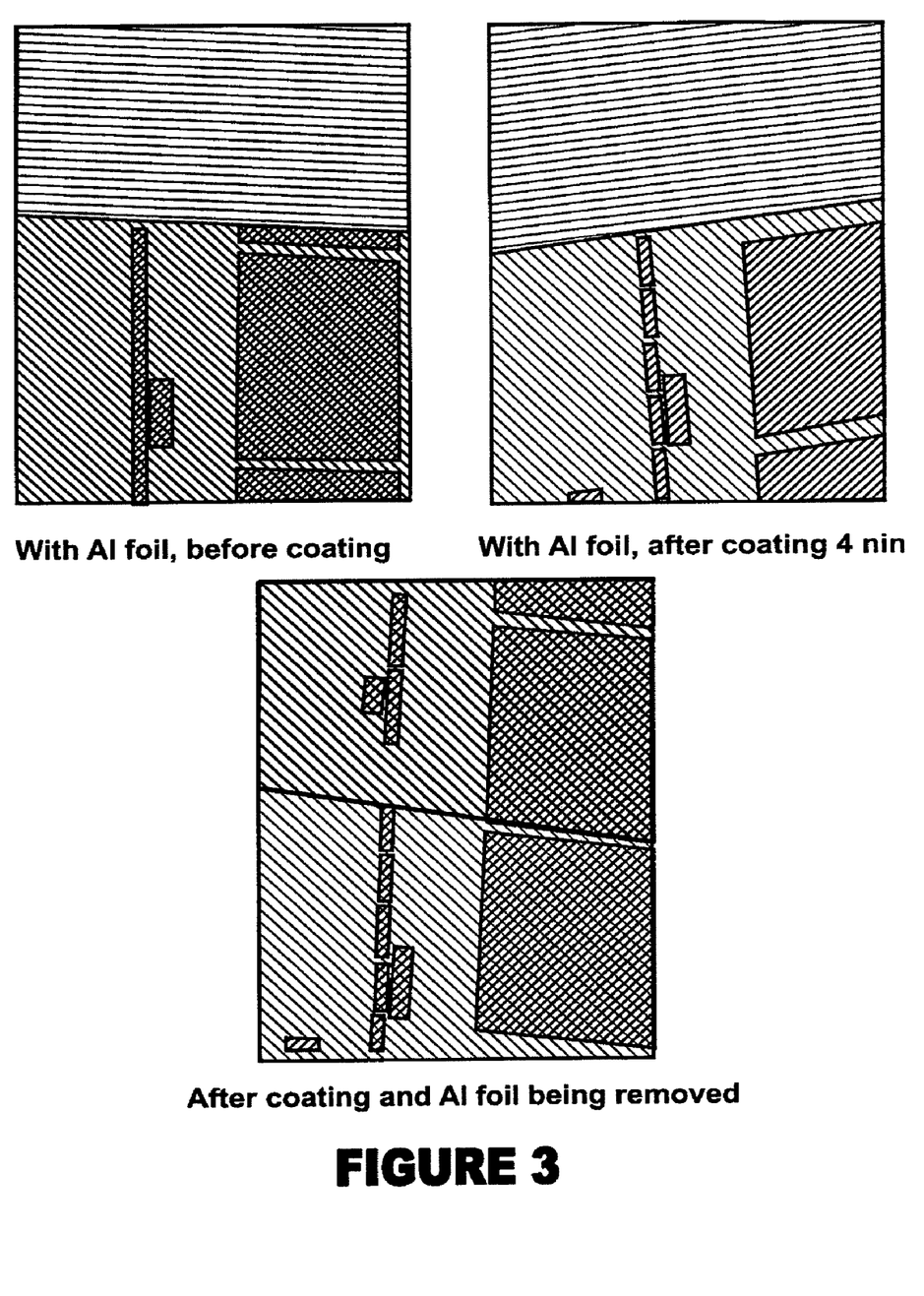
FIGS. 3 and 4 are top-view photographs of experimental results of a method according to an embodiment of the present invention.
Figure 4:
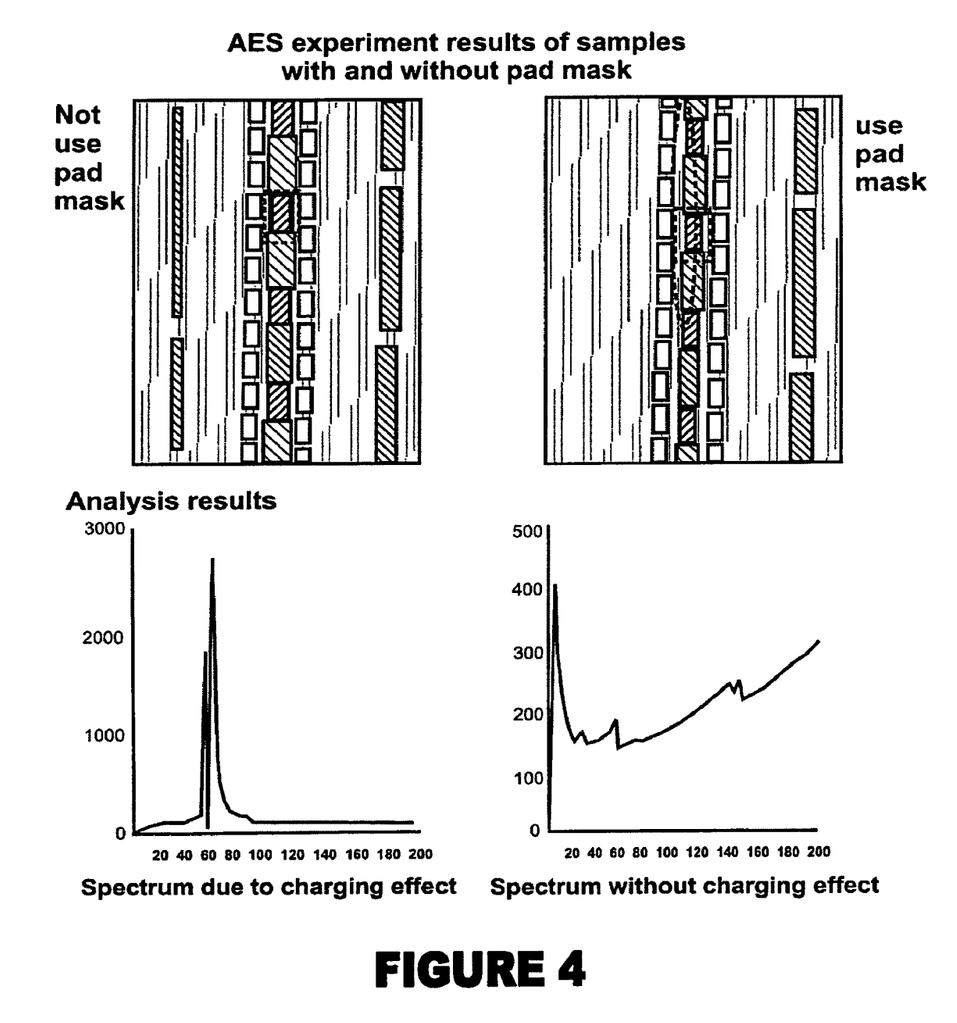

FIGS. 3 and 4 are top-view photographs of experimental results of a method according to an embodiment of the present invention. These diagrams are merely examples, which should not unduly limit the scope of the claims herein. One of ordinary skill in the art would recognize many variations, modifications, and alternatives. As shown, FIG. 3 shows sample pictures before and after platinum coating (with aluminum foil before coating, with aluminum foil after coating, and after coating and aluminum foil removed). FIG. 4 shows AES results of samples with and without Pt coating. As shown, the analysis without charging influences illustrates the various peaks, which are clean and easy to understand. Of course, there can be other variations, modifications, and alternatives.

Depending upon the embodiment, one or more of the following benefits can be achieved.
1. Simple, cost effective, effective for charge effect reduction;
2. No damage or interfering signals generated on the analyzed pad surface;
3. Save time for AES sample preparation.

Based on the method, we have designed a "Pad Mask Tool" to make the pad mask to analyze the pad surface according to a specific embodiment. Further details of the present tool can be found throughout the present specification and more particularly below.

Figure 5:
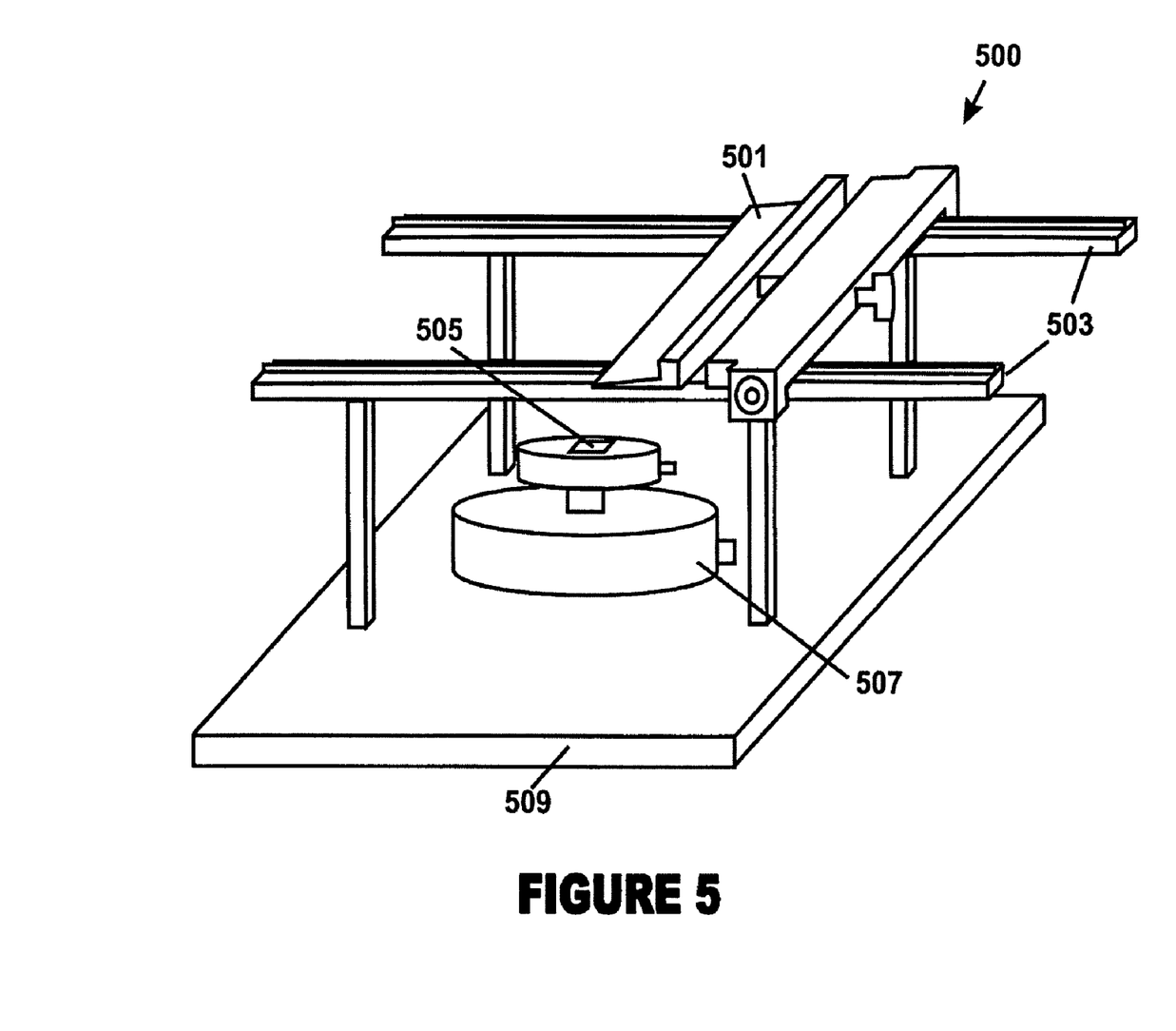
FIGS. 5 through 8 are illustrations of a pad mask tool according to embodiments of the present invention.
Figure 6:
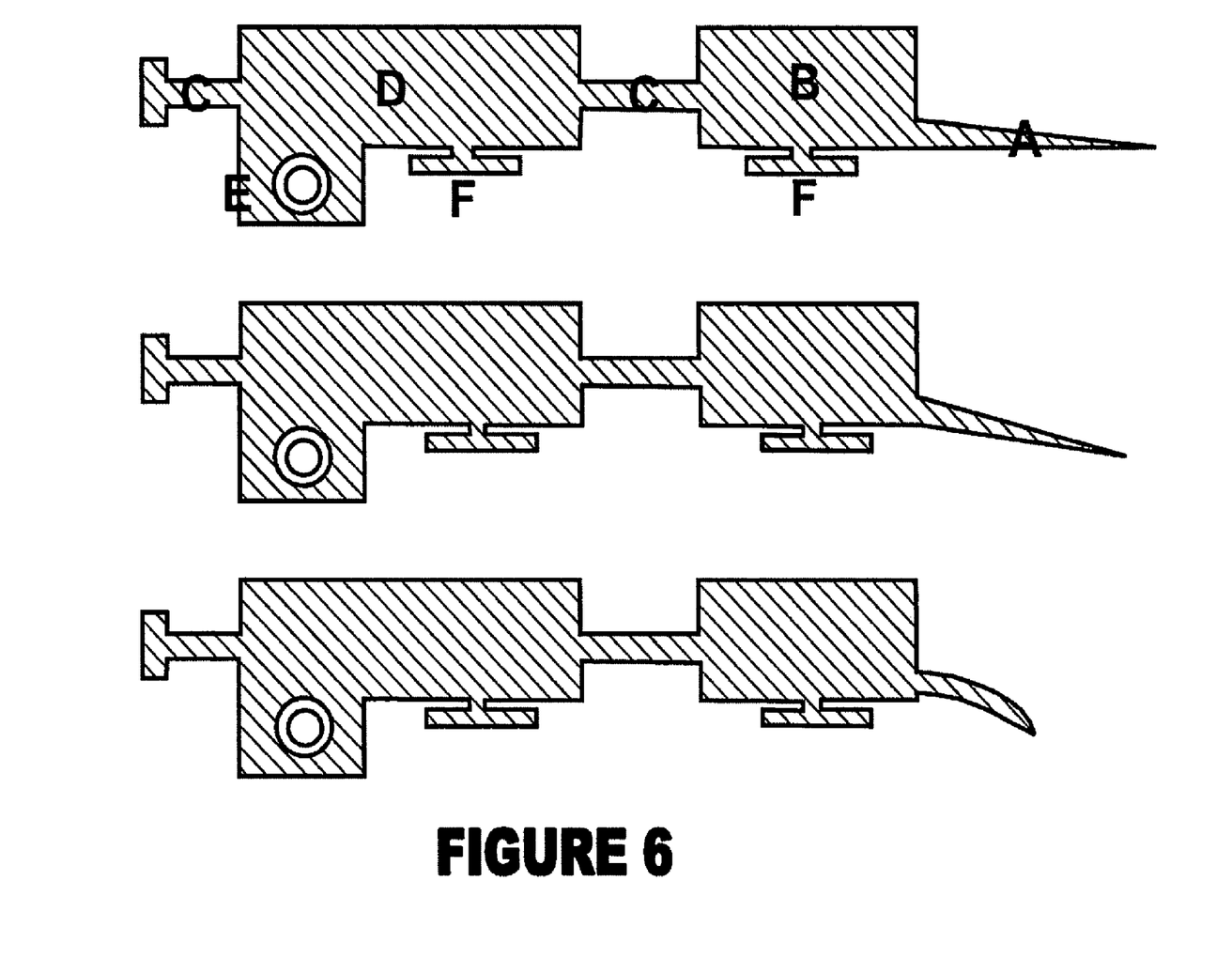
Figure 7:
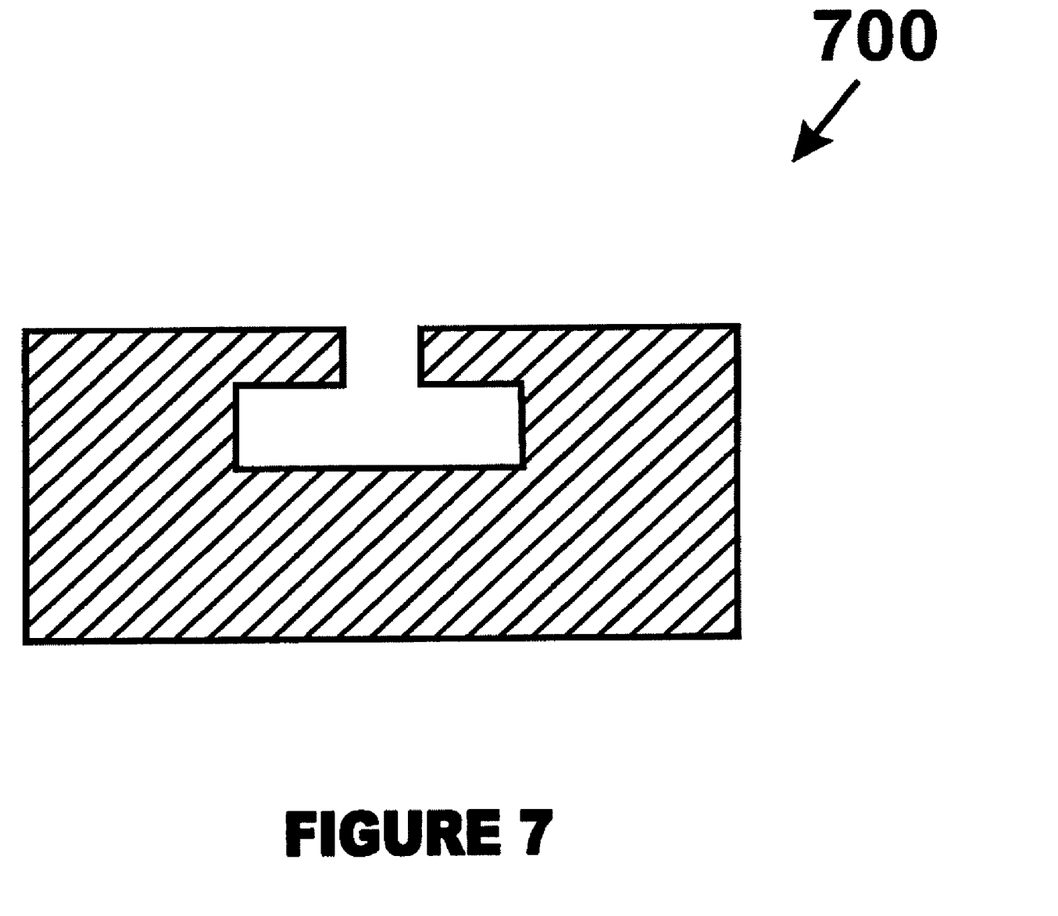

FIGS. 5 through 8 are illustrations of a pad mask tool according to embodiments of the present invention. These diagrams are merely examples, which should not unduly limit the scope of the claims herein. One of ordinary skill in the art would recognize many variations, modifications, and alternatives. As shown in FIG. 5, our Pad Mask Tool 500 is made up of at least four parts: shield 501, track 503, sample holder 505, 507, and pedestal 509 according to a specific embodiment. Referring to FIG. 6, the shield is composed of at least six parts: A, B, C, D, E, and F according to a specific embodiment. Depending upon the embodiment, the shield can include fewer or more parts. As shown, D is used to roughly move the shield on the track according to a specific embodiment. E is a screw and used for fix the shield on the track in a specific embodiment. C can be a screw or other mechanism according to a specific embodiment. Adjusting C can make sure B and D move relatively with precision according to a specific embodiment. A and B can be an integrated module or A is designed to insert into the groove on B according to an embodiment. A is the key parts of the shield, its front end must desirably be thin and hard enough. Its thickness can be ~5 um or other dimensions. There is no special shape required and it can be design as the illustrated shapes. F is used to fix the shield on track to move. The track is designed as the shape 700 in FIG. 7. There is groove opened on it for the inserting and moving of the part F of the shield.

Figure 8:
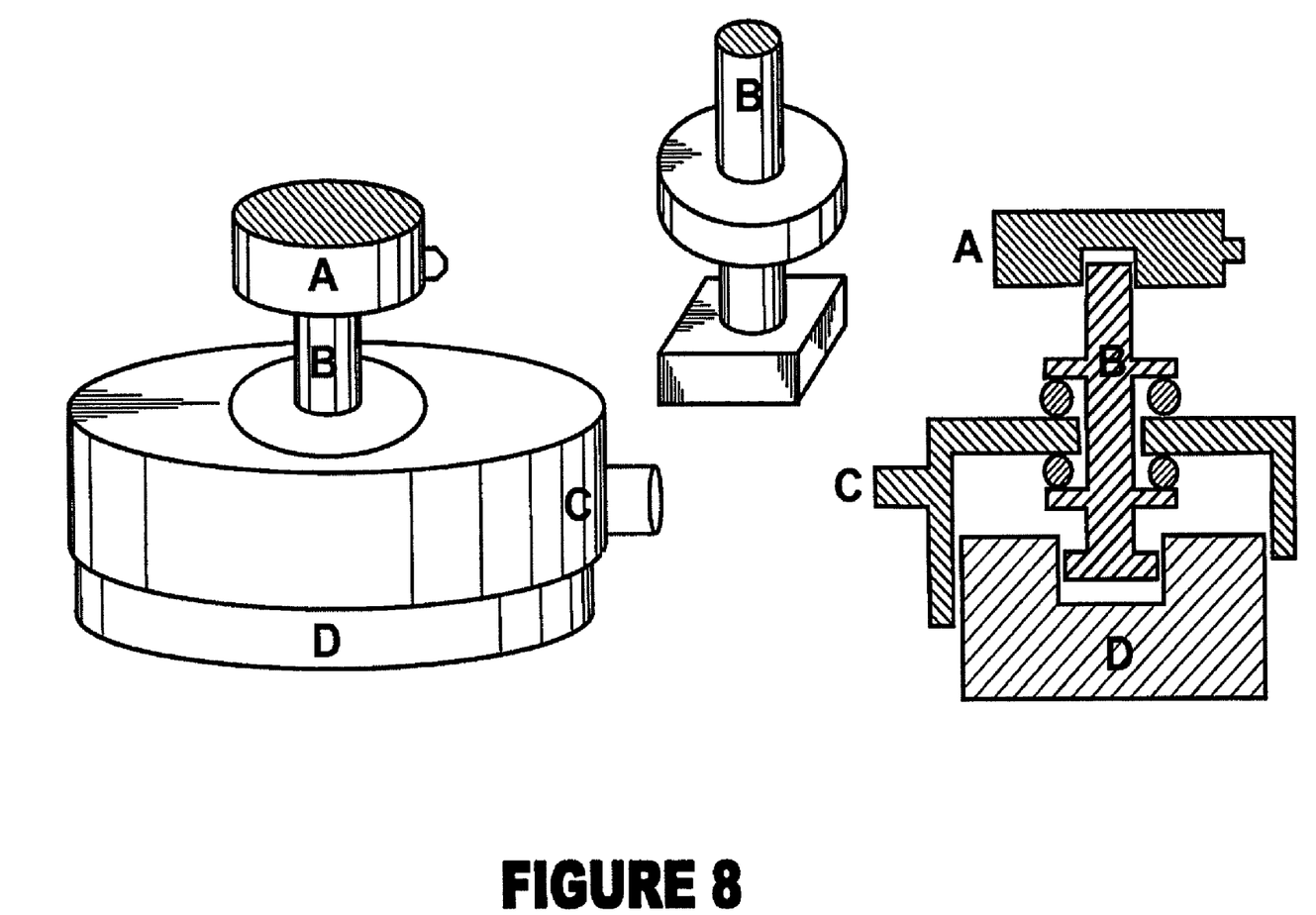

Referring now to FIG. 8, the sample stage is made up of four parts: A, B, C, and D according to a specific embodiment. They ensure the sample to be rotated at random and able to roughly or precisely move up and down according to a specific embodiment. The sample can be attached to A using double side stick tape or be clamped to A by designing a clamp on A. A can roughly move relative to B and also can rotate at random according to a specific embodiment. After moving or rotating to its right position, A can be fastened to B using a screw. B has a column structure with lower part square and upper part circle. Two circle plates are designed in its middle part. D is fixed on the pedestal and has one square hole on it. The square low part of B can be inserted into the hole without gap, which ensures B only be able to move up and down according to a specific embodiment. The joining between D and C is by screw and/or other attachment mechanism according to a specific embodiment. C has a handle on it. Rotating C can make it move precisely relative to D. The roller balls lying between B and C then gear B to move up and down. The precise up and down movement of the sample is thus realized. The pedestal is used to sustain and stabilize the entire pad mask tool, as shown. Of course, there can be other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for analyzing a sample for the manufacture of integrated circuits, the method comprising:
    providing an integrated circuit chip, the integrated circuit chip having a surface area with at least one region of interest;
    covering a first portion of the surface area including the region of interest using a blocking material;
    forming a metal layer on a second portion of the surface area, while the blocking material protects the first portion;
    removing the blocking material to expose the first portion of the surface area including the region of interest;
    subjecting the metal layer to a voltage differential to draw away one or more charged particles from the first portion of the surface area; and
    subjecting the surface area including the region of interest to spectrometer analysis.

2. The method of claim 1 wherein the one or more charged particles is one or more electrons.

3. The method of claim 1 wherein the voltage differential comprises a ground potential.

4. The method of claim 1 wherein the region of interest comprises a pad area, the pad area comprising aluminum.

5. The method of claim 1 wherein the region of interest is surrounded by a passivation material comprises a silicon nitride layer overlying a silicon oxide layer.

6. The method of claim 1 wherein the metal layer comprises a platinum material.

7. The method of claim 1 wherein the metal layer has a thickness of about 50 Angstroms.

8. The method of claim 1 wherein the blocking material is an aluminum film.

9. The method of claim 1 wherein the region of interest comprises a bonding pad.

10. The method of claim 1 wherein the region of interest includes a defect.

* * * * *